United States Patent
Tanaka et al.

(10) Patent No.: US 8,150,537 B2
(45) Date of Patent: Apr. 3, 2012

(54) TRANSCRANIAL ELECTRICAL STIMULATION DEVICE

(75) Inventors: Nobuhiro Tanaka, Hiroshima (JP); Kazuyoshi Nakanishi, Hiroshima (JP)

(73) Assignee: Hiroshima University, Hiroshima (JP)

( * ) Notice: Subject to any disclaimer, the term of this patent is extended or adjusted under 35 U.S.C. 154(b) by 106 days.

(21) Appl. No.: 12/667,131

(22) PCT Filed: Jul. 2, 2008

(86) PCT No.: PCT/JP2008/062021
§ 371 (c)(1),
(2), (4) Date: Aug. 26, 2010

(87) PCT Pub. No.: WO2009/005106
PCT Pub. Date: Jan. 8, 2009

(65) Prior Publication Data
US 2010/0324623 A1 Dec. 23, 2010

(30) Foreign Application Priority Data
Jul. 4, 2007 (JP) .................. 2007-176802

(51) Int. Cl.
*A61N 1/00* (2006.01)
(52) U.S. Cl. ....................................... 607/139
(58) Field of Classification Search .................. 607/139
See application file for complete search history.

(56) References Cited

U.S. PATENT DOCUMENTS

| 4,967,038 A * | 10/1990 | Gevins et al. ............... 600/383 |
| 5,332,401 A | 7/1994 | Davey et al. |
| 2008/0294031 A1* | 11/2008 | Wilson et al. ............... 600/383 |
| 2010/0036275 A1* | 2/2010 | Alkire ........................ 600/544 |

FOREIGN PATENT DOCUMENTS

| JP | 5-504492 | 7/1993 |
| JP | 07-289649 | 11/1995 |
| JP | 09-294815 | 11/1997 |
| JP | 2003-339885 | 12/2003 |

OTHER PUBLICATIONS

Int'l Search Report from corresponding Int'l Application No. PCT/JP08/062201 dated Jul. 29, 2008.

* cited by examiner

*Primary Examiner* — George Manuel
(74) *Attorney, Agent, or Firm* — Snell & Wilmer L.L.P.

(57) ABSTRACT

A transcranial electrical stimulation device 1 having a wearing equipment 2 detachably worn onto a patient's head and at least a pair of electrodes 4 attached to the wearing equipment 2, the device for electrically stimulating a motor area of a patient's cerebral cortex by outputting current from the electrode 4 connected to a current generator. An engagement part 6 capable of engaging the wearing equipment 2 to a scalp with a thread-like body 8 is provided to the wearing equipment 2, and the electrode 4 is attached to the wearing equipment 2 protrudably to the head side of the electrode 4, and tip of the electrode 4 is capable of subcutaneously piercing through the head. It is unnecessary to bore a patient's skull outer layer with a drill, and a mounting of the electrode can be performed in a short time. The electrodes can be accurately positioned at predetermined positions of a patient's head, and the motor area of a cerebral cortex can be effectively stimulated.

10 Claims, 3 Drawing Sheets

TRANSCRANIAL ELECTRICAL STIMULATION DEVICE

CROSS-REFERENCE TO RELATED APPLICATIONS

This application is U.S. national phase filing under 35 U.S.C. §371 of PCT/JP2008/062021 filed Jul. 2, 2008 and claims priority from Japanese Application No. 2007-176802 which was filed on Jul. 4, 2007.

TECHNICAL FIELD

The present invention relates to a transcranial electrical stimulation device capable of accurately positioning electrodes at predetermined positions of a patient's head and capable of effectively stimulating the motor area of a cerebral cortex.

BACKGROUND ART

A transcranial electrical stimulation method is a method for electrically stimulating the motor area of a cerebral cortex. The method was reported by Levy et al. in 1984 (Levy, 1984), and at the same time, the method was immediately spread all over the world.

The transcranial electrical stimulation method is widely used mainly for the purpose of spinal cord lesion segment diagnosis in a spinal cord disorder or for performing spinal cord function monitoring during surgery of a spinal cord tumor and the like (Mckay, 1997). Since spinal cord lesion segment diagnosis can functionally diagnose the lesion segment of the spinal cord disorder, the certainty of the treatment was dynamically improved.

When there is a danger of causing a spinal cord injury during a surgery of an intramedullary spinal cord tumor, scoliosis and the like, spinal cord function monitoring is essential for performing the surgery safely.

Regarding spinal cord lesion segment diagnosis or spinal cord function monitoring, there are many reports discussing its usefulness. With regard to the Applicant of the present application, there are 600 cases which had performed the transcranial electrical stimulation method in the past 12 years. When considering that there are approximately 4500 orthopedic hospitals in Japan, it is presumed that the number of cases in which the present method has been performed is large.

However, on the contrary, there also are problems such as the following.

In the conventional method, in order to stimulate the motor area of the cerebral cortex, the skull outer layer which is directly thereon is bored with a drill and a hole is made to mount a needle electrode.

Although there is no serious report for complications up till now in the conventional method, time was required to mount the electrode since the bone had to be bored.

Since there are personal differences in head size, it does not necessarily mean that an effective motor area of a cerebral cortex can be stimulated at the first electrode mounting. If an emission of an evoked potential is difficult, there are cases where a change in the electrode position is needed.

Therefore, a development is desired for a mounting means of an electrode which is more easily mountable to the head and is also minimally invasive.

Japanese Laid-Open Publication No. 9-294815 (Reference 1) discloses a transcranial electrical stimulation device for outputting currents which are independently adjusted, respectively, from two electrode pairs.

However, in this device, the electrodes are attached to the head by a band and the like. The electrodes cannot be accurately positioned to predetermined positions of a patient's head.

Japanese Laid-Open Publication No. 7-289649 (Reference 2) discloses a stimulant signal generating device of an ophthalmic nerve for generating nervous waves in which there is less weariness and the effect of the treatment is improved. However, this subject matter does not relate to a transcranial electrical stimulation device.

Japanese Laid-Open Publication No. 2003-339885 (Reference 3) discloses an electrical stimulating device for activating scalp capable of preventing the deterioration of scalp tissues, and reducing headache and symptoms accompanying therewith, by alleviating the abnormal tension of head part facial muscles. However, this subject matter also does not relate to a transcranial electrical stimulation device.

Reference 1: Japanese Laid-Open Publication No. 9-294815
Reference 2: Japanese Laid-Open Publication No. 7-289649
Reference 3: Japanese Laid-Open Publication No. 2003-339885

DISCLOSURE OF THE INVENTION

Therefore, the present invention may attain the following purposes.
(1) It is unnecessary to bore a patient's skull outer layer with a drill. Thus, a transcranial electrical stimulation device which can perform mounting of the electrode in a short time is provided.
(2) A transcranial electrical stimulation device capable of accurately positioning the electrodes at predetermined positions of a patient's head and capable of effectively stimulating the motor area of a cerebral cortex is provided.
(3) A transcranial electrical stimulation device having a mounting means of an electrode which is easily mountable to the head and is also minimally invasive is provided.

A transcranial electrical stimulation device of the present invention has a wearing equipment detachably worn on a patient's head and at least a pair of electrodes attached to the wearing equipment, and the device is for electrically stimulating a motor area of a patient's cerebral cortex by outputting current from the electrode connected to a current generator, wherein: an engagement part capable of engaging the wearing equipment to a scalp with a thread-like body is provided to the wearing equipment; and the electrode is attached to the wearing equipment protrudably to the head side, and tip of the electrode is capable of subcutaneously piercing through the head. Thus, the aforementioned purpose is attained.

In one embodiment, the engagement part is a through hole provided to the wearing equipment.

In one embodiment, a screw is formed around the electrode, and the electrode is screwed with the wearing equipment.

In one embodiment, the wearing equipment comprises an arch-shaped elastic member capable of an elastic deformation.

In one embodiment, the wearing equipment is a plate made of plastic and the like with elasticity.

In one embodiment, the wearing equipment has a hair band type shape.

In one embodiment, the thread-like body is a thread or string.

In one embodiment, a fastening part for securing the wearing equipment to a patient's head is provided to both sides of the wearing equipment.

In one embodiment, fixing equipment is fixed to the wearing equipment, and the electrode is attached, capable of screwing forward and backward to the fixing equipment.

In one embodiment, the electrode is movable in a longitudinal direction of the wearing equipment.

According to a transcranial electrical stimulation device of the present invention, when putting a thread through the engagement part (for example, hole) of the wearing equipment and sawing it to the scalp at the head top part of a patient to secure the engagement part to the head top part, the electrodes positioned both at left and right sides of the engagement part are positioned at predetermined positions, respectively, directed to a patient's cerebral cortex.

Thus, by outputting the current from the electrode, the motor area of a patient's cerebral cortex can be electrically stimulated.

In this way, by only wearing the wearing equipment on a patient's head, the electrodes can be accurately positioned at predetermined positions of a patient's head so that it can be effectively stimulating the motor area of a cerebral cortex. Since the distance between the electrode and the motor area of a patient's cerebral cortex is approximately constant, the motor area can be stimulated with a stable potential.

Since it is possible to generate sufficient stimulation by setting the electrode subcutaneously due to using a screw electrode, it is unnecessary to bore a patient's skull outer layer with a drill, and mounting of the electrode can be performed in a short time. Moreover, it is easily mountable to the head and is also minimally invasive.

Particularly, the transcranial electrical stimulation device being constituted by a hair band (one type of hair accessory) type base part and a needle electrode, the hair band type plate is made of plastic with elasticity. Thus, the transcranial electrical stimulation device of the present invention can be fit to the head in any kind of case without being affected by the shape and size of the head.

Moreover, the needle electrode is optimized such that it can effectively stimulate the cerebral cortex only by subcutaneously piercing without boring the skull outer layer. Additionally, if a plurality of holes for setting the needle electrode is formed on the hair band type base, a change in electrode position is very easy even if an effective stimulation of the motor area cannot be obtained.

BEST MODES FOR CARRYING OUT THE INVENTION

The embodiments of the present invention are described with reference to the drawings.

As shown in FIGS. 1-4, a transcranial electrical stimulation device 1 comprises a wearing equipment 2 which is detachably worn on a patient's head, and at least a pair of electrodes 4 attached to the wearing equipment 2.

The wearing equipment 2 comprises an arch-shaped plate capable of an elastic deformation. The wearing equipment 2 can be formed of an electrical insulating plastic with elasticity, and also can be constituted by a metal plate and the like. When forming the wearing equipment 2 with a metal plate, it is preferable to cover the surface of the metal plate with an electrical insulating resin.

Fastening parts 12 for securing the wearing equipment 2 onto a patient's head can be provided to both ends of the wearing equipment 2. The fastening parts 12 can be constituted by a sheet-like fastener. In that case, a chin strap having a sheet-like fastener provided to both ends is used. By fastening the sheet fastener of the chin strap to the fastening parts 12 of the wearing equipment 2, the wearing equipment 2 can be secured to the head.

Figure 7:
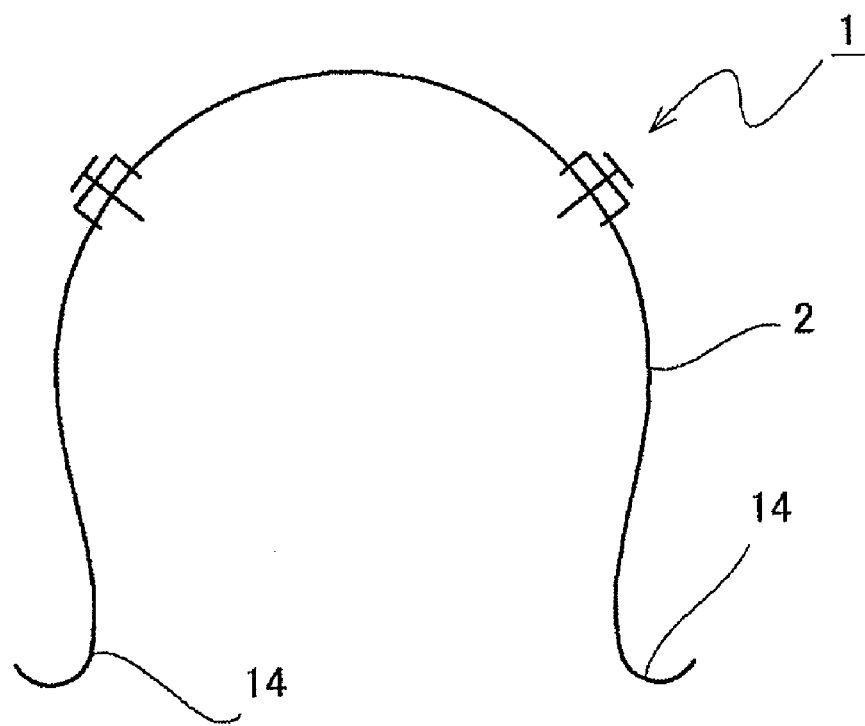
FIG. 7 is a diagram of another embodiment of an transcranial electrical stimulation device.

As shown in FIG. 7, curved parts 14 may be provided to both ends of the wearing equipment 2 such that the wearing equipment 2 can be attached to or detached from the ears or both sides of the head.

An engagement part 6 capable of engaging the wearing equipment 2 to a patient's scalp with a thread-like body 8 is provided to an approximate central part in a horizontal direction of the wearing equipment 2. The thread-like body 8 can be constituted by a thread or string.

The engagement part 6 may be a through-hole or a protrusion provided to the wearing equipment 2. The position of the through-hole 6 is provided to a place where the through-hole 6 is positioned at the head top part when wearing the wearing equipment 2 onto the head.

A pair of electrodes 4,4 are attached to the wearing equipment 2. When constituting the wearing equipment 2 with an arch-shaped plate, the electrodes 4 are attached to fixing parts 10 which are fixed to an outer surface of the plate.

The fixing appliances 10 are constituted into a disc-shape with an electrical insulating resin and the like, and holes 11 are formed at the central parts thereof. Through-holes (not shown) are formed on the plate of the wearing equipment 2 corresponding to the holes 11.

The electrode 4 is formed with a screw, and by screwing it into the hole 11 of the fixing equipment 10 and the hole of the wearing equipment 2, the electrode 4 is attached by having the protruding dimension towards the head adjustable.

Figure 4:
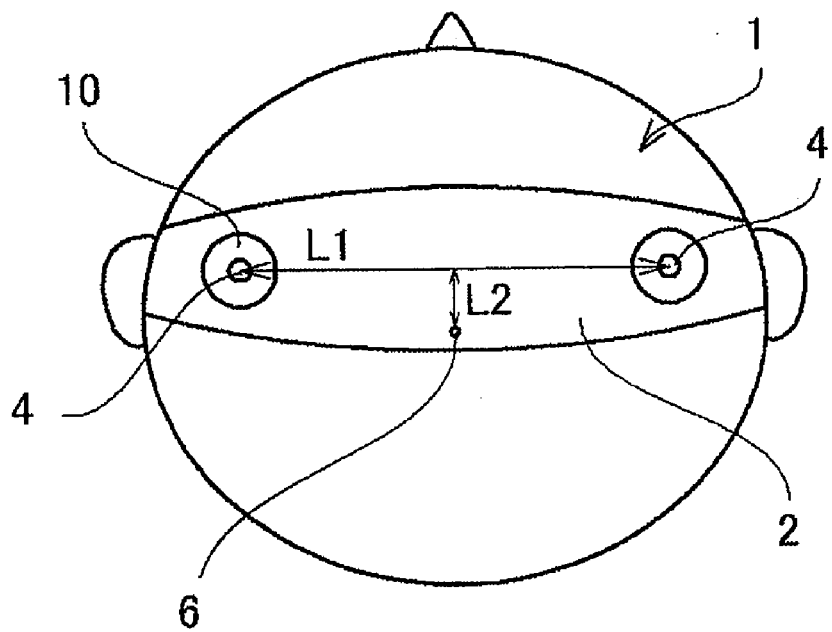
FIG. 4 is a top view showing a mounting condition of the condition of a transcranial electrical stimulation device of FIG. 1.
Figure 5:
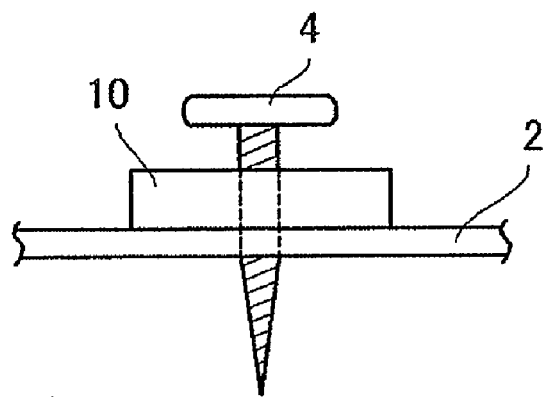
FIG. 5 is an enlarged view of a part of the transcranial electrical stimulation device of FIG. 1.
Figure 6:
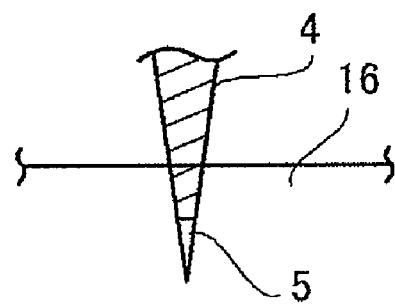
FIG. 6 is an explanation view showing a condition that the electrode of the transcranial electrical stimulation device is inserted a cerebral cortex.

As shown in FIG. 4, it is preferable to provide the electrode 4 to a position which is 4.5-5.5 cm apart in a horizontal direction (L1) and 1.5-2.5 cm apart in a forward direction (L2) with respect to the engagement part 6. Typically, it is provided to a position which is 5 cm apart in a horizontal direction and 2 cm apart in a forward direction with respect to the engagement part 6. When applying the stimulation device of the present invention to a child, a pair of electrodes 4,4 may be provided to a position which is horizontally 3 cm from the engagement part 6. These dimensions can be arbitrarily set by considering the size, sex, age and the like of a patient's head.

By positioning the engagement part 6 of the wearing equipment 2 at the top of a patient's head, the electrode 4 is directed to the motor area of a patient's cerebral cortex.

A female screw corresponding to a male screw of the electrode 4 may be formed inside the hole of the fixing equipment 10.

The screw is not provided to the tip 5 of the electrode 4, and it is approximately conical or conical trapezoid.

Materials for electrodes to be used may include those which are conventionally known. For example, platinum, silver, copper, stainless, gold or a matter which is a gold-plated conductor may be used. Particularly, gold and gold-plated matters are preferable.

The pair of electrodes 4 is connected to a conventionally known current generator (not shown) with a code. The motor area of a patient's cerebral cortex can be electrically stimulated by outputting currents from the electrodes 4. The current generator generates currents including pulses. A controlling means for adjusting and controlling the currents is connected to the current generator, and the controlling means adjusts the current amplitude, pulse duration, pulse frequency and the like.

Next, a method for electrically stimulating the motor area of a patient's cerebral cortex using the transcranial electrical stimulation device 1 of the aforementioned configuration is described.

Figure 1:
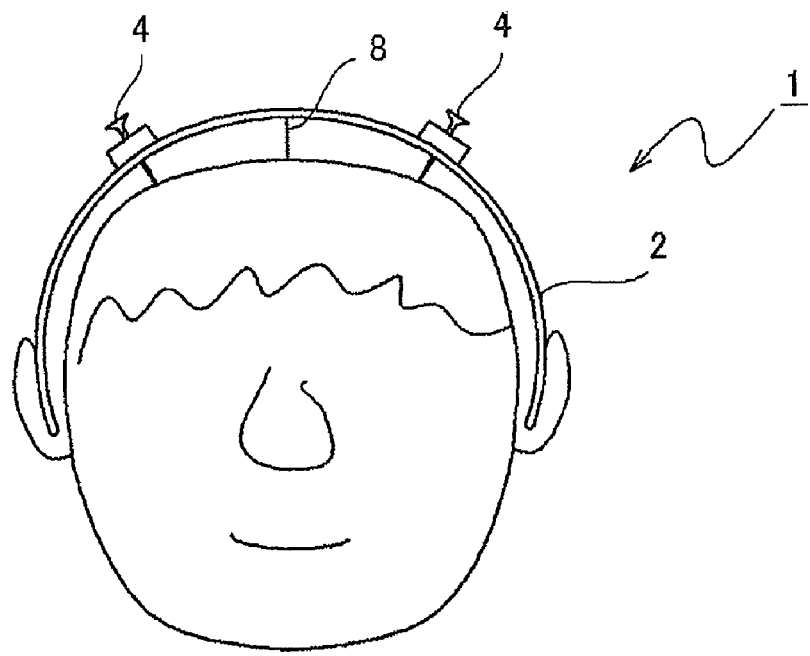
FIG. 1 is an explanation view showing a condition of a transcranial electrical stimulation device which is worn on a patient's head of one embodiment of the present invention.
Figure 2:
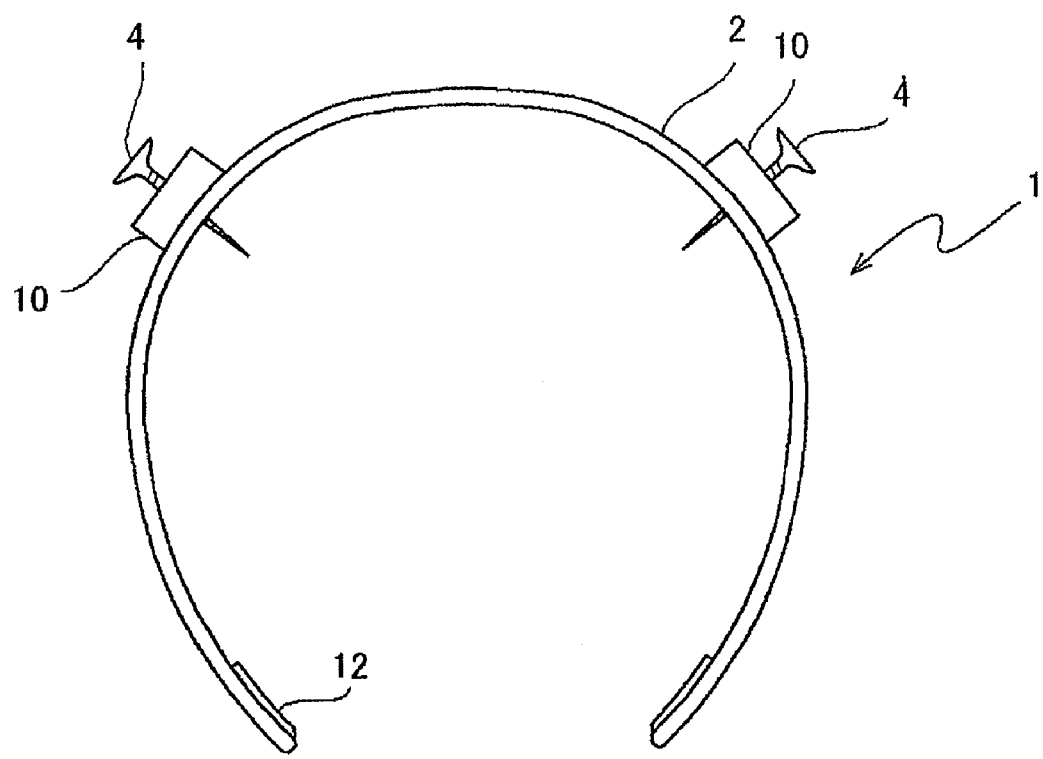
FIG. 2 is a front view of the condition of a transcranial electrical stimulation device of FIG. 1.
Figure 3:
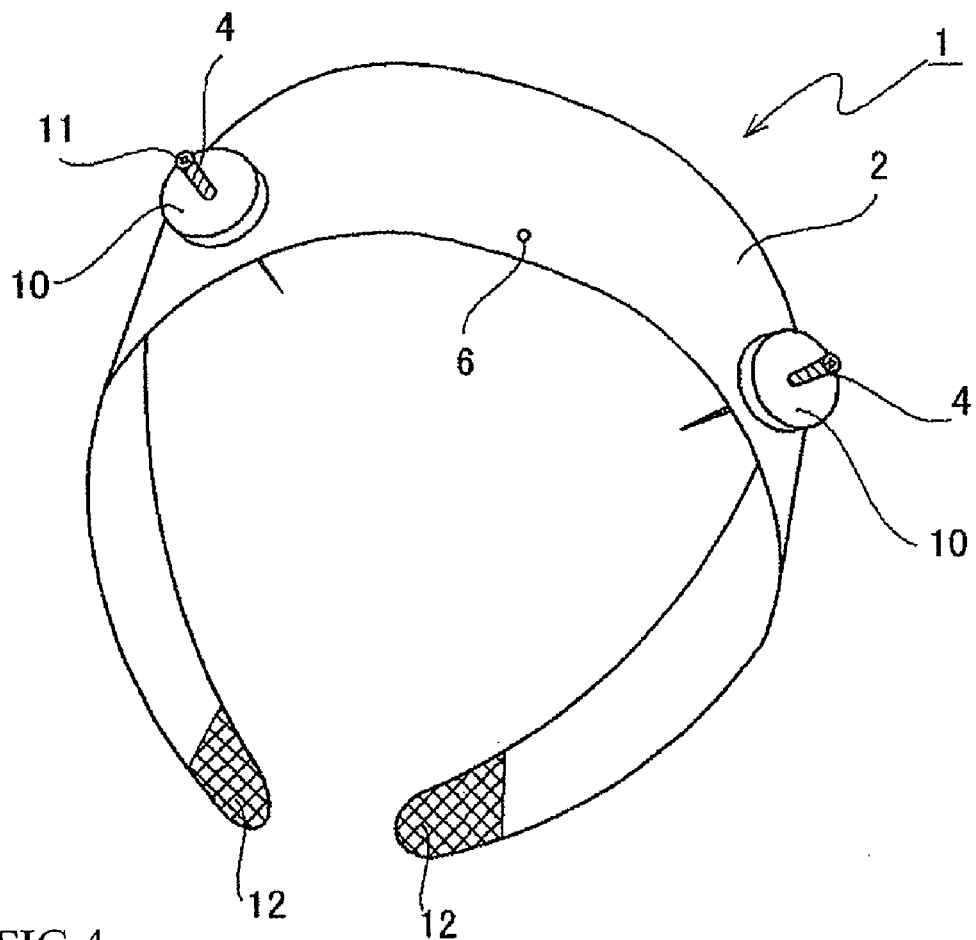
FIG. 3 is a perspective view of the condition of a transcranial electrical stimulation device of FIG. 1.

As shown in FIGS. 1 and 4, the wearing equipment 2 is mounted to a patient's head. Herein, when providing fastening parts 12 to both ends of the wearing equipment 2, the tightening member such as a band, strap or string is under the patient's chin to secure the fastening parts 12. Since the wearing equipment 2 is elastic, it can adapt to various sizes of the patients' heads.

A thread 8 is put through the through-hole 6 provided to the wearing equipment 2 to saw it into the scalp at the top of a patient's head. Due to this, the central part of the wearing equipment 2 is nearly secured to the top of a patient's head. Simultaneously, the positions of both electrodes 4,4 are positioned at predetermined locations of a patient's head.

Next, the electrode 4 is rotated to proceed the tip 5 subcutaneously 16. As the electrode 4 protrudes towards the head, the wearing equipment receives a counteraction and tries to draw away from the head. However, the central part of the wearing equipment 2 is secured with a thread 8 and the like at the top of the head as described above. Thus, the central part of the wearing equipment 2 does not greatly separate from the head, and accordingly, the tip of the electrode 4 is inserted subcutaneously.

The tip part of the electrode 4 is inserted subcutaneously 16 for approximately 4-5 mm. Herein, since the screw is formed around the electrode 4, the electrode 4 contacts the subcutaneous tissue of the head by a wide contact area. In this state, the current is output from the electrode 4 connected to the current generator to electrically stimulate the motor area of a patient's cerebral cortex.

In this way, by outputting the current from the electrode 4 in a state where the electrode 4 is sufficiently in contact with the subcutaneous tissue, the cerebral cortex can be effectively stimulated.

In the aforementioned embodiment, holes for setting the electrodes 4 to the wearing equipment 2 were formed at two places at both sides of the engagement part 6. However, they may be formed at several places. Moreover, the electrodes may be constituted according to the head size, sex and age such that they move along the plate of the wearing equipment. For example, a long hole may be provided to the plate of the wearing equipment to slidably stop the electrode at the long hole.

INDUSTRIAL APPLICABILITY

According to the present invention, it is unnecessary to bore a patient's skull outer layer with a drill. Thus, a transcranial electrical stimulation device which can perform mounting of the electrode in a short time is provided. The device is capable of accurately positioning the electrodes at predetermined positions of a patient's head and capable of effectively stimulating the motor area of a cerebral cortex. The device is easily mountable to the head and is also minimally invasive.

The invention claimed is:

1. A transcranial electrical stimulation device having a wearing equipment detachably worn onto a patient's head and at least a pair of electrodes attached to the wearing equipment, the device for electrically stimulating a motor area of a patient's cerebral cortex by outputting current from the electrode connected to a current generator, wherein:

an engagement part capable of engaging the wearing equipment to a scalp with a thread-like body is provided to the wearing equipment; and the electrode is attached to the wearing equipment protrudably to the head side, and tip of the electrode is capable of subcutaneously piercing through the head.

2. A transcranial electrical stimulation device according to claim 1, wherein the engagement part is a through hole provided to the wearing equipment.

3. A transcranial electrical stimulation device according to claim 1, wherein a screw is formed around the electrode, and the electrode is screwed with the wearing equipment.

4. A transcranial electrical stimulation device according to claim 1, wherein the wearing equipment comprises an arch-shaped elastic member capable of an elastic deformation.

5. A transcranial electrical stimulation device according to claim 4, wherein the wearing equipment is a plate made of plastic.

6. A transcranial electrical stimulation device according to claim 1, wherein the wearing equipment has a hair band type shape.

7. A transcranial electrical stimulation device according to claim 1, wherein the thread-like body is a thread or string.

8. A transcranial electrical stimulation device according to claim 1, wherein a fastening part for securing the wearing equipment to a patient's head is provided to both sides of the wearing equipment.

9. A transcranial electrical stimulation device according to claim 1, wherein a fixing equipment is fixed to the wearing equipment, and the electrode is attached capable of screwing forward and backward to the fixing equipment.

10. A transcranial electrical stimulation device according to claim 1, wherein the electrode is movable in a longitudinal direction of the wearing equipment.

* * * * *